United States Patent [19]
Blackburn et al.

[11] Patent Number: 5,663,409
[45] Date of Patent: Sep. 2, 1997

[54] PROCESS FOR THE PREPARATION OF 3-(METHYLTHIO) PROPANAL AND 2-HYDROXY-4-(METHYLTHIO) BUTANENITRILE

[75] Inventors: Thomas F. Blackburn, Chesterfield; Paul F. Pellegrin, St. Louis, both of Mo.

[73] Assignee: Novus International, Inc., St. Louis, Mo.

[21] Appl. No.: 476,356

[22] Filed: Jun. 7, 1995

[51] Int. Cl.$^6$ .................... C07C 253/30; C07C 253/00; C07C 319/18; C07C 323/22

[52] U.S. Cl. .................................. 558/351; 568/41

[58] Field of Search .................. 568/41; 558/351

[56] References Cited

U.S. PATENT DOCUMENTS

| | | | |
|---|---|---|---|
| 2,521,677 | 9/1950 | Vander Weele | 260/601 |
| 2,523,633 | 9/1950 | Pierson et al. | 260/601 |
| 2,542,768 | 2/1951 | Gresham et al. | 260/465.6 |
| 2,557,913 | 6/1951 | Livak et al. | 260/309.5 |
| 2,584,496 | 2/1952 | Pierson et al. | 260/601 |
| 2,626,282 | 1/1953 | Cunningham et al. | 260/601 |
| 2,676,190 | 4/1954 | Bernard et al. | 260/601 |
| 2,745,745 | 5/1956 | Blake et al. | 99/4 |
| 2,776,996 | 1/1957 | Hunt et al. | 260/601 |
| 2,938,053 | 5/1960 | Blake et al. | 260/561 |
| 3,438,868 | 4/1969 | Sawaki et al. | 203/8 |
| 3,529,940 | 9/1970 | Shima et al. | 23/288 |
| 3,574,766 | 4/1971 | Meyer et al. | 260/601 |
| 3,699,148 | 10/1972 | Darcas et al. | 260/465.6 |
| 3,833,651 | 9/1974 | Ouchi et al. | 260/534 S |
| 3,878,057 | 4/1975 | Mannsfeld | 203/35 |
| 4,048,232 | 9/1977 | Koberstein et al. | 260/601 R |
| 4,225,516 | 9/1980 | Biola et al. | 568/41 |
| 4,319,047 | 3/1982 | Komora et al. | 568/41 |
| 5,352,837 | 10/1994 | Hsu et al. | 568/41 |

FOREIGN PATENT DOCUMENTS

| | | |
|---|---|---|
| 797873 | 10/1968 | Canada . |
| 820968 | 8/1969 | Canada . |
| 976673 | 3/1951 | France . |
| 50-4018 | 1/1975 | Japan . |
| 867966 | 5/1961 | United Kingdom . |
| 986198 | 3/1965 | United Kingdom . |
| 1150252 | 4/1969 | United Kingdom .......... C07C 149/14 |
| 1162054 | 8/1969 | United Kingdom .......... C07C 149/14 |
| 1166961 | 10/1969 | United Kingdom .......... C07C 149/14 |
| 1173174 | 12/1969 | United Kingdom .......... C07C 145/14 |
| 1177470 | 1/1970 | United Kingdom .......... C07C 149/14 |
| 1510256 | 5/1978 | United Kingdom .......... C07C 149/14 |

OTHER PUBLICATIONS

Chemical Abstracts, vol. 53, No. 18, Sep. 25, 1959, Abstract No. 16940b for Z. Brzozowski, "Preparation of β–methylthiopropionaldehydes," Roczniki Chem., vol. 33, pp. 217–220 (1959).

Chemical Abstracts, vol. 82, No. 3, Jan. 20, 1975, Abstract No. 16318p for Japanese Patent No. 74024890, Jun. 26, 1974.

Chemical Abstracts, vol. 83, No. 1, Jul. 7, 1975, Abstract No. 9197r for Japanese Patent No. 74024046, Jun. 20, 1974.

Derwent World Patent Index abstract for Japanese Patent No. No. 74024890, Jun. 26, 1974.

Derwent World Patent Index Patent No. 74024046, Jun. 20, 1974.

Z. Brzozowski, "Preparation of β–methylthiopropionaldehydes," Roczniki Chem., vol. 33, pp. 217–220, 91959).

*Primary Examiner*—Johann Richter
*Assistant Examiner*—Laura L. Stockton
*Attorney, Agent, or Firm*—Senniger, Powers, Leavitt & Roedel

[57] ABSTRACT

Catalytic processes for the preparation of 3-(methylthio) propanal and 2-hydroxy-4-(methylthio)butanenitrile using novel addition catalysts are disclosed. The novel addition catalysts include: nicotinamide, imidazole, benzimidazole, 2-fluoropyridine, poly-4-vinylpyridine, 4-dimethylaminopyridine, picoline and pyrazine.

17 Claims, No Drawings

PROCESS FOR THE PREPARATION OF 3-(METHYLTHIO) PROPANAL AND 2-HYDROXY-4-(METHYLTHIO) BUTANENITRILE

BACKGROUND OF THE INVENTION

The present invention relates to catalytic processes for the preparation of 3-(methylthio)propanal (hereinafter "MMP") and 2-hydroxy-4-(methylthio)butanenitrile ("HMBN"). More particularly, the present invention relates to processes for preparing MMP and HMBN using novel addition catalysts.

MMP and HMBN are intermediates for the manufacture of both d,l-methionine and 2-hydroxy-4-(methylthio) butanoic acid ("HMBA"). Methionine is an essential amino acid commonly deficient in grains used in animal feed compositions. HMBA provides a source of methionine, and is widely used as a methionine supplement in animal feed formulations.

MMP is produced by the catalytic reaction between acrolein and methyl mercaptan. In a conventional process for the preparation of MMP, liquid acrolein and methyl mercaptan are introduced into a reactor containing liquid phase MMP and a suitable organic base which acts as an olefin/mercaptan addition reaction catalyst. Reaction takes place in the liquid phase. Conventional organic base catalysts for the reaction between acrolein and methyl mercaptan include amines such as pyridine, hexamethylenetetramine and triethylamine. The olefin/mercaptan addition reaction catalyst is typically combined with an organic acid such as acetic acid to inhibit polymerization of acrolein and improve product yield.

HMBN is subsequently produced by the addition reaction between MMP and hydrogen cyanide in the presence of a suitable addition reaction catalyst, which may include the organic bases used to catalyze the reaction between acrolein and methyl mercaptan. Methionine may be produced by reacting HMBN with excess ammonia under high pressure to produce 2-amino-4-(methylthio)butanenitrile and subsequently hydrolyzing the product using a mineral acid to form methionine. Alternatively, methionine may be produced by reacting MMP with ammonium carbonate to form a hydantoin and subsequently hydrolyzing the hydantoin with a base to form methionine. HMBA may be produced by hydrolyzing HMBN using a mineral acid.

Pyridine has proven to be an effective addition catalyst used in preparing both MMP and HMBN. However, it would be highly beneficial to identify effective alternative addition reaction catalysts for the preparation of these valuable intermediates.

SUMMARY OF THE INVENTION

Among the several objects of the present invention are the provision of a process for the preparation of MMP by the catalytic reaction between acrolein and methyl mercaptan; the provision of such a process which provides a high MMP reaction yield; the provision of such a process in which the degradation of MMP and production of high molecular weight by-products is maintained at acceptably low levels; the provision of such a process which can produce high quality MMP that can be used directly, without the need for further purification, in the preparation of methionine or HMBA; the provision of a process for the preparation of HMBN by the catalytic reaction between the MMP reaction product and hydrogen cyanide; the provision of such a process which provides a high HMBN reaction yield; and the provision of such a process in which the catalyst remaining in the MMP reaction product may be further used to catalyze the reaction between MMP and hydrogen cyanide to produce HMBN.

Briefly, therefore, the present invention is directed to a process for the manufacture of MMP. The process comprises reacting methyl mercaptan with acrolein in a reaction zone in the presence of a novel olefin/mercaptan addition reaction catalyst. The novel catalyst comprises at least one organic base selected from the group consisting of nicotinamide, imidazole, benzimidazole, 2-fluoropyridine, 4-dimethylaminopyridine, picoline and pyrazine.

It has been further discovered that the novel olefin/mercaptan addition reaction catalyst used in catalyzing the reaction between acrolein and methyl mercaptan are also useful in catalyzing the reaction between MMP and hydrogen cyanide to produce HMBN. Thus, the present invention is further directed to a process for the manufacture of HMBN comprising reacting MMP with hydrogen cyanide in the presence of an addition reaction catalyst. The addition reaction catalyst comprises at least one organic base selected from the group consisting of nicotinamide, imidazole, benzimidazole, 2-fluoropyridine, poly-4-vinylpyridine, 4-dimethylaminopyridine, picoline and pyrazine.

In accordance with another embodiment of the present invention, the novel addition catalyst disclosed herein are used to first catalyze the reaction between methyl mercaptan and acrolein to produce an intermediate reaction product mixture comprising MMP and the novel catalyst. Then, without prior separation of the catalyst from the MMP in the intermediate reaction product mixture, the MMP reaction product is reacted with hydrogen cyanide to produce HMBN.

Other objects and features of this invention will be in part apparent and in part pointed out hereinafter.

DETAILED DESCRIPTION OF THE PREFERRED EMBODIMENTS

In accordance with the present invention, MMP is produced by the reaction between acrolein and methyl mercaptan in the presence of novel olefin/mercaptan addition catalysts. MMP in the reaction product mixture may then be reacted with hydrogen cyanide to produce HMBN using the novel catalysts present in the MMP reaction product mixture as addition reaction catalyst in the cyanidation reaction.

The catalytic reaction between acrolein and methyl mercaptan to produce MMP is well-known and, in the practice of the present invention, this reaction can be carried out in any suitable fashion without particular limitation to the various process conditions employed. For example, acrolein vapor may be absorbed in a liquid reaction medium containing recycled MMP product. The acrolein absorbed in the liquid reaction medium is reacted with methyl mercaptan in the presence of an olefin/mercaptan addition reaction catalyst within the reaction zone of a suitable reactor. Methyl mercaptan is added to the liquid reaction medium in an amount at least substantially stoichiometrically equivalent to the acrolein on a molar basis. A slight excess of methyl mercaptan may be employed. Preferably, about 1 to about 1.02 moles of methyl mercaptan are introduced into the reaction zone for each mole of acrolein present in the liquid reaction medium. The methyl mercaptan and acrolein can be introduced into the liquid reaction medium either simultaneously or successively. The olefin/mercaptan addition reaction catalyst may be present either completely or partially in the MMP or can be introduced into the liquid reaction medium entirely or partially along with the acrolein and methyl mercaptan.

The temperature of the reaction is desirably maintained within the range from about 30° to about 70° C. Reaction pressure is not critical and may vary within wide limits. However, in order to simplify the reaction apparatus, it is preferred that the reaction be conducted at about atmospheric pressure or at only moderately reduced or elevated pressure.

The reaction between acrolein and methyl mercaptan may be conducted in either a continuous or batchwise fashion. In a batch process, acrolein vapor or liquid may be added to methyl mercaptan in substantially molar equivalent quantities. Alternatively, acrolein and methyl mercaptan may be simultaneously introduced at substantially stoichiometrically equivalent rates of addition into a liquid reaction medium comprising MMP. The reaction medium for a given batch is conveniently provided for a given batch by leaving a heel of MMP in the reactor from a previous batch. Thus, the batch reactor may be operated in a semi-continuous mode in which the acrolein and methyl mercaptan are introduced at a substantially constant rate over a significant portion of the batch cycle, and the reaction product is periodically withdrawn from the reactor, leaving a heel for the next batch.

Fully continuous processes are described, for example, in Biola U.S. Pat. No. 4,225,516 and Hsu et al. U.S. Pat. No. 5,352,837, both of which are expressly incorporated herein by reference. As described in Hsu et al., the continuous reaction may be carried out by introducing acrolein vapor and methyl mercaptan into a flowing MMP reaction medium in either a co-current or countercurrent gas/liquid contact zone. Alternatively, the initial reaction may be carried out in a stirred tank reactor having an external cooler through which the reaction mixture is circulated. If the reaction is not completed in the residence time afforded in the initial gas/liquid contact zone, the MMP reaction medium containing unreacted acrolein and methyl mercaptan is forwarded to a second reactor (e.g., a plug flow reactor or a batch holding tank) for completion of the reaction. Preferably, the reaction temperature of the reaction does not exceed about 70° C. in any of the reaction zones.

Olefin/mercaptan addition catalysts for the commercial production of MMP are preferably evaluated on the basis of several criteria, including (1) conversion and yield of MMP; (2) reaction kinetics; and (3) tendency to catalyze unwanted side reactions which produce high molecular weight by-products and decrease product purity, both during the MMP reaction and during subsequent storage of the MMP reaction product. Furthermore, such catalysts are preferably useful in further catalyzing the reaction between MMP and hydrogen cyanide to produce HMBN so that the MMP reaction product mixture containing the addition catalyst can be directly treated with hydrogen cyanide to produce HMBN, without intervening purification.

It has been discovered that certain organic bases which previously had not been recognized as viable olefin/mercaptan addition reaction catalyst may advantageously be used to catalyze the reaction between acrolein and methyl mercaptan to form MMP. Accordingly, the novel catalyst of the present invention includes at least one organic base selected from the group consisting of nicotinamide, imidazole, benzimidazole, 2-fluoropyridine, 4-dimethylaminopyridine, picoline (e.g., 2-picoline, 3-picoline and 4-picoline) and pyrazine.

Each of these organic bases may suitably be used as olefin/mercaptan addition catalyst in the commercial production of MMP. However, with reference to the catalyst evaluation criteria identified herein, some of these organic bases have demonstrated greater overall performance and effectiveness than others. In accordance with a more preferred embodiment of the present invention, the olefin/mercaptan addition catalyst comprises at least one organic base selected from the group consisting of imidazole, benzimidazole and picoline.

In addition to the aforementioned organic bases, we have considered other organic bases as olefin/mercaptan addition reaction catalyst for use in the preparation of MMP, including poly-4-vinylpyridine, tripropylamine, tributylamine, triphenylamine, tribenzylamine, t-octylamine, sodium nicotinamide and 3-fluoropyridine. In addition to these base catalysts, we have also contemplated using certain salts as catalyst for promoting the reaction between acrolein and methyl mercaptan, including alkali metal acetates, molybdates and formates, either alone or combined with a crown ether or quaternary ammonium salt to enhance the solubility of the salt anion in the MMP reaction mixture, zinc acetate, zinc carbonate and salts of ethylenediaminetetraacetic acid. Furthermore, we have examined the use of other compounds, viz., p-toluenesulfonic acid, 4-aminobutyric acid and palladium chloride, as catalysts in the preparation of MMP.

The olefin/mercaptan addition reaction catalyst should be present in the liquid reaction medium in an amount sufficient to effectively catalyze the reaction between acrolein and methyl mercaptan. Preferably, the molar ratio of the catalyst to methyl mercaptan present in the reaction zone is from about 0.001 to about 0.02.

It should be noted that some of the novel olefin/mercaptan addition reaction catalyst disclosed herein (e.g., nicotinamide, imidazole, benzimidazole and poly-4-vinylpyridine) are solids at typical MMP reaction temperatures. If sufficiently soluble, such solid catalysts may be suitably employed by dissolving the catalyst in the liquid MMP reaction mixture. If the catalyst is insufficiently soluble, a minimal amount of a suitable solvent (e.g., water) may be added to the reaction mixture as a catalyst solubility aid, or the catalyst may simply be suspended in the reaction mixture.

The novel olefin/mercaptan addition reaction catalysts described herein are preferably combined with an organic or inorganic acid in the reaction zone. The presence of an acid is believed to moderate the basicity of the organic liquid reaction medium, thereby inhibiting undesirable base-catalyzed side reactions which decrease MMP quality. Moreover, the acid may enhance the solubility of solid catalysts in the liquid MMP reaction mixture. A variety of organic acids may be used, including acetic acid, formic acid, citric acid, short-chain fatty acids and organic sulfo-acids (e.g., trifluoromethanesulfonic acid). Suitable inorganic acids include mineral acids such as sulfuric and phosphoric acid. Due to commercial availability and relatively low cost, acetic acid is preferred. The molar ratio of organic base to acetic acid introduced into the reaction zone is typically from about 0.5 to about 2.0. Preferably, in order to ensure that base-catalyzed side reactions are sufficiently inhibited, the molar ratio of organic base to acetic acid introduced into the reaction zone is from about 0.5 to about 1.0. Where one or more of the aforementioned bases is combined in the reaction zone with a mineral acid, the mineral acid is preferably sulfuric acid or phosphoric acid. The molar ratio of the organic base to the mineral acid introduced into the reaction zone is preferably from about 1 to about 50. When one of the organic bases disclosed herein is combined with an organic or inorganic acid in the reaction zone, the liquid reaction medium preferably contains between about 0.2 and about 0.75 weight percent of the organic base/acid combination.

MMP reaction product may be used directly for the preparation of HMBN without prior distillation for removal of either high boiling or low boiling impurities. This not only saves the capital and operating expense of distillation, but also avoids the yield losses inevitably resulting from the formation of additional high boilers in an MMP distillation column. HMBN may be produced by reacting the MMP reaction product with hydrogen cyanide in the presence of a suitable addition reaction catalyst. Advantageously, it has been further discovered that nicotinamide, imidazole, benzimidazole, 2-fluoropyridine, poly-4-vinylpyridine, 4-dimethylaminopyridine, picoline and pyrazine may serve as addition reaction catalyst in the production of HMBN.

Thus, in accordance with a preferred embodiment of the present invention, it is possible to first prepare MMP by reacting methyl mercaptan with acrolein in a reaction zone in the presence of one of the novel olefin/mercaptan addition reaction catalysts disclosed herein, either alone or in combination with a suitable organic or inorganic acid, to produce an intermediate reaction product mixture containing MMP and the catalyst. Thereafter, and without prior separation of the catalyst from the MMP in the intermediate reaction product mixture, the MMP can be directly converted to HMBN by reacting the MMP with hydrogen cyanide.

The catalytic reaction between MMP and hydrogen cyanide to produce HMBN is well-known and, in the practice of the present invention, this reaction can be carried out in any suitable fashion without particular limitation to the various process conditions employed. The MMP product may be reacted with hydrogen cyanide in either a continuous or batchwise reaction system. Preferably, hydrogen cyanide is present in a slight molar excess of about 2 percent relative to MMP. The temperature of the cyanidation reaction is desirably maintained within the range from about 30° to about 70° C., preferably from about 50° to about 70° C. As in the MMP reaction, the pressure maintained during the cyanidation reaction is not critical and may vary within wide limits, but preferably is close to atmospheric pressure.

Due to their overall effectiveness as catalysts for both the olefin/mercaptan addition reaction and the reaction between MMP and hydrogen cyanide, the addition catalyst used to prepare HMBN in this fashion preferably comprises at least one organic base selected from the group consisting of imidazole, benzimidazole and picoline.

The MMP and hydrogen cyanide must be reacted in the presence of a sufficient amount of addition catalyst to effectively promote the cyanidation reaction. For some catalyst systems, a greater quantity of addition catalyst may be employed during the cyanidation reaction than is present during the reaction between acrolein and methyl mercaptan. Thus, an excess of addition catalyst may be used initially during the MMP reaction in order to insure that a sufficient quantity of catalyst is present in the intermediate reaction product mixture to effectively catalyze the reaction between MMP and hydrogen cyanide. However, using an excess of addition catalyst in the reaction between acrolein and methyl mercaptan to later achieve optimal hydrogen cyanide addition may cause excessive degradation of the MMP reaction product. In such cases, it is preferred that an additional amount of an organic base catalyst be introduced into the intermediate reaction product mixture immediately prior to the introduction of hydrogen cyanide to further promote the cyanidation reaction. The catalyst added to the intermediate reaction product mixture may be selected from any of the novel addition catalysts disclosed herein and may, in fact, be the same catalyst used to catalyze the reaction between acrolein and methyl mercaptan. Alternatively the added catalyst may comprise a conventional organic base catalyst (e.g., pyridine, triethylamine, hexamethylenetetramine etc.). Preferably, prior to the introduction of the additional catalyst, the intermediate reaction product mixture contains between about 0.01 and about 1 weight percent, more preferably, between about 0.05 and about 0.25 weight percent of the addition catalyst, and after the additional amount of catalyst is introduced into the intermediate reaction product mixture, the intermediate reaction product mixture contains between about 0.05 and about 1 weight percent, more preferably, between about 0.1 and about 0.5 weight percent of addition catalyst.

The HMBN produced by the process of the present invention may be directly converted without purification to HMBA by either the process described in Ruest et al. U.S. Pat. No. 4,524,077 or the process of Hernandez U.S. Pat. No. 4,912,257. In the process of the Ruest patent, HMBN is hydrolyzed in sulfuric acid, the HMBA product extracted from the hydrolyzate using a substantially water-immiscible solvent, and the extract steam-distilled to produce an 85 to 90% by weight aqueous solution of HMBA. In the process of the Hernandez patent, the hydrolyzate is neutralized with ammonia, causing it to separate into two phases, the organic phase being evaporated and filtered to produce an 85 to 90% aqueous solution of HMBA.

The present invention is illustrated by the following Examples which are merely for the purpose of illustration and are not to be regarded as limiting the scope of the invention or manner in which it may be practiced.

EXAMPLE 1

The following procedure was used in this Example to assess performance of proposed olefin/mercaptan catalysts for the reaction between acrolein and methyl mercaptan to produce MMP.

The catalyst to be tested was mixed with acrolein and a quantity of this mixture was combined with an excess of methyl mercaptan in a 2 ml reaction vial with septum cap. Methyl mercaptan was transferred using dry ice cooling of both the mercaptan vial and the reaction vial. An excess of methyl mercaptan of about 5 to 15 weight percent based on acrolein was employed. The amount of catalyst present in the reaction vial was chosen to provide approximately 0.0033 moles of catalyst per mole of acrolein or MMP product. In some tests, the catalyst was combined with an organic or inorganic acid in a molar ratio of approximately 0.7 (catalyst to acid). Also, water was sometimes added to the mixture in the reaction vial to improve catalyst solubility. Where a salt catalyst was employed, it was sometimes combined with a crown ether or a quaternary ammonium salt in a substantially equivalent molar proportion to the salt to improve catalyst solubility.

The reaction vial containing the mixture was held in an oven maintained at about 50° C. After approximately 30 minutes, the reaction vial was removed and reweighed to determine weight loss during heating (normally less than about 0.002 g). Samples of the reaction mixture contained in the vial were analyzed by gas chromatography for assay and to determine the amount of high molecular weight oligomers present in the mixture.

Table 1 contains a summary of the performance of the alternative aldehyde reaction catalysts which were evaluated using the above-described procedure. Control tests using pyridine and pyridine combined with acetic acid are included for purposes of comparison. Criteria for evaluating catalyst performance included acrolein conversion, amounts of high molecular weight oligomers and qualitative assessment of the appearance of the appropriate chromatogram. Ideally, the MMP reaction mixture contained in the vial will show a low acrolein concentration (indicating high conversion to MMP), low amounts of high molecular weight oligomers (indicating minimal side reactions), and a generally flat gas chromatography base line (indicating the absence of other polymers). Poor quality material will have a pronounced broad peak eluting several minutes after the aldehyde peak, which does not always correlate with oligomer levels. Gas chromatography-mass spectroscopy work has shown this broad peak to be aldehyde, indicating other components are breaking down in the analysis to form this peak. Since in this procedure an excess of methyl mercaptan was used, aldehyde yield was not considered a meaningful evaluation criterion.

In Table 1, the gas chromatography baseline codes (S), (M) and (U) indicate satisfactory, marginal and unsatisfactory, respectively. ND and tr indicate "not detected" and "trace", respectively. All values are reported as weight percent.

TABLE 1

| MMP Catalyst (GC assay Baseline Code) | Acrolein | High Molecular Weight oligomers |
| --- | --- | --- |
| Pyridine (S) | 0.5 | 9.6 |
| Pyridine/acetic acid (S) | 0.1 | 0.1 |
| Imidazole/acetic acid (S) | tr | 1.1 |
| Imidazole/acetic acid (S) | 0.3 | 1.8 |
| Benzimidazole/water/acetic acid (S) | 0.2 | 1.0 |
| Nicotinamide (U) | 0.3 | 1.7 |
| Nicotinamide (U) | 0.9 | 6.5 |
| Nicotinamide (U) | 0.4 | 3.0 |
| Nicotinamide/water (U) | ND | 0.2 |
| Nicotinamide/water (U) | 0.3 | 5.0 |
| Nicotinamide/acetic acid (S) | 5.2 | |
| Nicotinamide/acetic acid/water (S) | 0.7 | 2.8 |
| Nicotinamide/acetic acid/water (S) | ND | 4.0 |
| Nicotinamide/water/sulfuric acid (U) | 1.6 | tr |
| Nicotinamide/water/sulfuric acid (U) | ND | 5.0 |
| Nicotinamide/water/sulfuric acid (U) | 2.8 | <0.1 |
| Nicotinamide/water/phosphoric acid (U) | 0.5 | 4.4 |
| Sodium nicotinamide (U) | | 14.6 |
| Sodium nicotinamide/acetic acid (U) | ND | 4.9 |
| Poly-4-vinylpyridine (U) | | 8.1 |
| Poly-4-vinylpyridine/acetic acid (U) | 0.1 | 1.2 |
| Poly-4-vinylpyridine/acetic acid (U) | 0.1 | 2.2 |
| Poly-4-vinylpyridine/acetic acid (U) | 0.1 | |
| Sodium acetate/15-crown-5 (M) | 2.0 | 24.8 |
| Sodium acetate/trioctylmethylammonium chloride (U) | 1.3 | 4.4 |
| Sodium molybdate (U) | 0.1 | 4.7 |
| Sodium molybdate/acetic acid (U) | 0.3 | 7.5 |
| Sodium Formate (U) | <0.1 | 0.3 |

TABLE 1-continued

| MMP Catalyst (GC assay Baseline Code) | Acrolein | High Molecular Weight oligomers |
| --- | --- | --- |
| Disodium EDTA (U) | 13.1 | 1.3 |
| Disodium EDTA/acetic acid (U) | ND | 2.3 |
| Palladium chloride (U) | ND | 0.3 |
| p-Toluenesulfonic acid (U) | ND | 5.8 |
| 4-Aminobutyric acid (U) | ND | 2.3 |
| 4-Aminobutyric acid/acetic acid (U) | ND | 2.8 |
| 4-Aminobutyric acid/acetic acid/water (U) | ND | 2.7 |
| 2-Fluoropyridine/acetic acid (S) | 0.1 | <0.1 |
| 3-Fluoropyridine/acetic acid (U) | 0.2 | <0.1 |
| Tripropylamine/acetic acid/water (U) | <0.1 | <0.1 |
| Tributylamine/acetic acid (U) | <0.1 | 0.5 |
| Triphenylamine (U) | <0.1 | <0.1 |
| Triphenylamine/acetic acid (U) | <0.1 | 0.2 |
| Tribenzylamine (U) | 0.2 | <0.1 |
| Pyrazine/acetic acid (U) | <0.1 | 0.1 |
| t-Octylamine/acetic acid (U) | 0.2 | 2.0 |
| 4-Dimethylaminopyridine/acetic acid (S) | <0.1 | 0.5 |
| 4-Dimethylaminopyridine/acetic acid/water (S) | 0.1 | 0.9 |
| Zinc acetate (U) | 0.4 | 0.4 |
| Zinc carbonate (U) | 0.3 | <0.1 |

EXAMPLE 2

In this Example, nicotinamide, imidazole, benzimidazole, 2-fluoropyridine, pyrazine and 4-picoline were tested using the procedure described below to further assess their performance as olefin/mercaptan addition catalysts for the reaction between acrolein and methyl mercaptan.

Distilled acrolein having a typical assay of about 97.3 to about 97.5 weight percent acrolein and about 2.5 weight percent water was mixed with hydroquinone to provide a mixture having a hydroquinone concentration of about 0.10 to about 0.12 weight percent. The mixture of distilled acrolein and hydroquinone was stored at 0° to 5° C. Distilled methyl mercaptan having a typical assay of about 99.3 to about 99.5 weight percent methyl mercaptan was employed.

The aldehyde reaction was conducted in a 1000 ml stainless steel reactor with internal cooling coils for temperature control and an agitator. A quantity of MMP was first prepared by reacting acrolein and methyl mercaptan in the presence of a particular aldehyde catalyst. This MMP was then used as a "heel" in preparing a subsequent batch of MMP using the same catalyst. Typically, several batches of MMP were prepared using the same catalyst and an MMP heel from the preceding batch so that steady state conditions were approached.

To make the MMP heel, methyl mercaptan was charged to the reactor followed by the catalyst using a subsurface feed tube. The reactor and its contents were warmed to ambient temperature at which time the acrolein was fed to the reactor over a period of about 25 minutes at a reaction temperature of about 50° C. About 1.005 moles of methyl mercaptan and about 0.0033 moles of catalyst were charged to the reactor per mole of acrolein. Except in the case of nicotinamide, the catalyst in the reactor was combined with acetic acid using a molar ratio of about 0.7 (catalyst to acetic acid). The aldehyde reaction was finished by maintaining the process temperature at about 50° C. and agitating the contents of the reactor for about 60 minutes. Once the aldehyde reaction was complete, the reactor and its contents were cooled to 20° to 25° C. over a period of about 10 minutes while continuing agitation.

The catalyst (0.0033 moles per mole of acrolein) and, except in the case of nicotinamide, acetic acid (0.7 catalyst to acetic acid molar ratio) were blended with the MMP heel and charged to the reactor for preparation of additional aldehyde. Methyl mercaptan and acrolein were then fed simultaneously to the reactor with agitation over a period of about 30 minutes at a reaction temperature of about 60° C. Approximately 1.005 moles of methyl mercaptan per mole of acrolein were charged to the reactor. The aldehyde reaction was finished by maintaining the process temperature at about 60° C. for about 23 minutes. Once the aldehyde reaction was complete, the reactor and its contents were cooled to 20° to 25° C. over a period of about 10 minutes. If necessary, the batch reaction sequence was repeated using a particular catalyst and an MMP heel from the preceding batch until steady state conditions were approached.

A sample of the reaction mixture from the final batch was injected into a gas chromatograph for assay. A sample of this reaction mixture was also subjected to gas chromatography analysis to determine the amounts of high molecular weight oligomers in the mixture. In some cases, limited aging studies of the MMP reaction product were carried out to test storage stability.

Table 2 contains a summary of the performance of the alternative aldehyde reaction catalysts which were evaluated using the above-described procedure. The results in Table 2 include the weight percent of methyl mercaptan, acrolein, MMP and high molecular weight oligomers in the final batch reaction mixture. The results from a control test using a pyridine catalyst combined with acetic acid are included for purposes of comparison.

TABLE 2

| MMP Catalyst | MeSH | Acrolein | MMP | High Molecular Weight Oligomers |
|---|---|---|---|---|
| Pyridine/acetic acid | 0.30 | 0.23 | 97.88 | 1.25 |
| Nicotinamide | 0.94 | 0.5 | 89.74 | 9.47 |
| Imidazole/acetic acid | 0.11 | 0.5 | 97.12 | 1.43 |
| Benzimidazole/acetic acid/water | 0.21 | 0.17 | 97.59 | 1.56 |
| 2-Fluoropyridine/ acetic acid | 0.64 | 0.5 | 96.50 | 2.12 |
| Pyrazine/acetic acid | 0.30 | 0.23 | 97.88 | 2.19 |
| 4-picoline/ acetic acid | 0.21 | 0.38 | 98.02 | 1.14 |

Of the catalysts evaluated in this Example, nicotinamide, pyrazine, and 2-fluoropyridine produced MMP having elevated levels of high molecular weight oligomers.

The MMP produced using imidazole, benzimidazole and 4-picoline as catalysts was tested for storage stability at 45° C. For purposes of comparison, MMP made using pyridine combined with acetic acid was also aged at 45° C. to assess storage stability. In a typical aging study, 40 g of the aldehyde product were placed in a glass bottle which was then transferred to an oven maintained at 45° C. Periodically, samples of the product were withdrawn from the bottle and analyzed by gas chromatography for assay. The results from the MMP aging study are summarized in Table 3.

TABLE 3

| MMP Catalyst | Days | MMP Loss (wt % MMP/day) |
|---|---|---|
| Pyridine/acetic acid | 30 | 0.10 |
| Imidazole/acetic acid | 11 | 3.98 |
| Benzimidazole/acetic acid | 11 | 1.05 |
| 4-picoline/acetic acid | 10 | 0.30 |
| 4-picoline/acetic acid | 21 | 0.37 |
| 4-picoline/acetic acid | 31 | 0.37 |

At 45° C., MMP produced using imidazole, benzimidazole and 4-picoline as olefin/mercaptan addition catalysts showed faster deterioration as compared to aldehyde made using pyridine.

The MMP prepared using imidazole, benzimidazole and 4-picoline combined with acetic acid as olefin/addition reaction catalysts was converted to HMBN by reacting it with hydrogen cyanide using the organic base catalyst remaining in the MMP reaction product mixture to further catalyze the cyanidation reaction. For purposes of comparison, the MMP prepared using pyridine/acetic acid as the catalyst was also converted to HMBN.

The nitrile reaction was conducted in the same 1000 ml stainless steel reactor with agitator and internal cooling coils for temperature control. The MMP charge containing the organic base catalyst was first weighed into the reactor. Hydrogen cyanide (99.5%) was then fed to the reactor with agitation over a period of 26 minutes at a temperature of about 60° C. Approximately 1.02 moles of hydrogen cyanide per mole of MMP were charged to the reactor. The nitrile reaction was finished by holding the batch without agitation or cooling for about 20 minutes. Once the nitrile reaction was complete, the reactor and its contents were cooled to 20° to 25° C. over a period of about 10 minutes. A sample of the reaction mixture was subjected to gas chromatographic analysis to determine its assay, MMP and oligomer content. The results from the nitrile conversion are summarized in Table 4.

TABLE 4

| HMBN Catalyst | MMP | HMBN | High Molecular Weight Oligomers |
|---|---|---|---|
| Pyridine/acetic acid | ND | 98.5 | 0.7 |
| Imidazole/acetic acid | tr | 98.3 | 1.2 |
| Benzimidazole/ acetic acid | ND | 94.7 | 1.3 |
| 4-picoline/acetic acid | ND | 99.3 | 0.7 |

EXAMPLE 3

Distilled acrolein and methyl mercaptan were used to prepare an MMP heel and batch after the manner of Example 2. Poly-4-vinylpyridine, supplied by Reilley (Reillex 425) was used as the olefin/mercaptan addition reaction catalyst. Poly-4-vinylpyridine (2.7 g) was charged to the empty reactor. Methyl mercaptan (88.4 g) was then charged to the reactor. The reactor and its contents were warmed to ambient temperature at which time acrolein (100.9 g) was fed to the reactor over a period of about 50 minutes at a reaction temperature of about 50° C. The aldehyde reaction was finished as described in Example 2. Without further catalyst addition, methyl mercaptan (196.1 g) and acrolein (235.9 g) were then fed simultaneously to the reactor with agitation over a period of about 50 minutes at a reaction temperature of about 50° C. The aldehyde reaction was finished by maintaining the process temperature at about 50° C. for about 30 minutes. A sample of the reaction mixture from the batch was subjected to gas chromatographic analysis. The analysis showed 89.9% MMP, 0.4% acrolein, 0.8% methyl mercaptan, and 0.02% pyridine.

The MMP product containing the poly-4-vinylpyridine catalyst was converted to the nitrile in the same reactor after the manner of Example 2. Hydrogen cyanide (155.4 g) was fed to the reactor containing MMP (600.0 g) with agitation over a period of about 50 minutes at a temperature of about 50° C. The nitrile reaction was finished by holding the batch without agitation or cooling for about 30 minutes. Once the nitrile reaction was complete, the reactor and its contents were cooled to 20°–25° C. over a period of about 10 minutes. A sample of the nitrile reaction mixture was subjected to gas chromatographic analysis. The analysis showed 72.9% HMBN and 2.6% MMP.

In view of the above, it will be seen that the several objects of the invention are achieved. As various changes could be made in the above-described processes without departing from the scope of the invention, it is intended that all matter contained in the above description be interpreted as illustrative and not in a limiting sense.

What is claimed is:

1. A process for the manufacture of 3-(methylthio) propanal comprising reacting methyl mercaptan with acrolein in a reaction zone in the presence of an olefin/mercaptan addition reaction catalyst, said catalyst comprising at least one organic base selected from the group consisting of imidazole, benzimidazole, 2-fluoropyridine, 4-dimethylaminopyridine, picoline and pyrazine.

2. A process as set forth in claim 1 wherein said olefin/mercaptan addition reaction catalyst comprises at least one organic base selected from the group consisting of imidazole, benzimidazole and picoline.

3. A process as set forth in claim 1 wherein the molar ratio of organic base to methyl mercaptan introduced into said reaction zone is from about 0.001 to about 0.02.

4. A process as set forth in claim 3 wherein said olefin/mercaptan addition reaction catalyst is combined with an organic acid in said reaction zone.

5. A process as set forth in claim 4 wherein said organic acid is acetic acid and the molar ratio of said organic base to acetic acid introduced into said reaction zone is from about 0.5 to about 2.0.

6. A process as set forth in claim 5 wherein said reaction zone contains a liquid reaction medium comprising 3-(methylthio)propanal and said catalyst, said liquid reaction medium containing between about 0.2 and about 0.75 weight percent of said catalyst/organic acid combination.

7. A process as set forth in claim 3 wherein said olefin/mercaptan addition reaction catalyst is combined with a mineral acid in said reaction zone.

8. A process as set forth in claim 7 wherein said mineral acid is selected from the group consisting of sulfuric acid and phosphoric acid and the molar ratio of said olefin/mercaptan addition reaction catalyst to said mineral acid introduced into said reaction zone is from about 1 to about 50.

9. A process as set forth in claim 8 wherein said reaction zone contains a liquid reaction medium comprising 3-(methylthio)propanal and said catalyst, said liquid reaction medium containing between about 0.2 and about 0.75 weight percent of said catalyst/mineral acid combination.

10. A process for the manufacture of 2-hydroxy-4-(methylthio)butanenitrile comprising:

reacting methyl mercaptan with acrolein in a reaction zone in the presence of an olefin/mercaptan addition reaction catalyst comprising at least one organic base selected from the group consisting of imidazole, benzimidazole, 2-fluoropyridine, 4-dimethylaminopyridine, picoline and pyrazine, thereby producing an intermediate reaction product mixture comprising 3-(methylthio)propanal and said catalyst; and without prior separation of said catalyst from the 3-(methylthio)propanal of said intermediate reaction product mixture, reacting said 3-(methylthio)propanal with hydrogen cyanide to produce 2-hydroxy-4-(methylthio)butanenitrile.

11. A process as set forth in claim 10 wherein said olefin/mercaptan addition reaction catalyst is combined with acetic acid in said reaction zone.

12. A process as set forth in claim 10 wherein said olefin/mercaptan addition reaction catalyst comprises at least one organic base selected from the group consisting of imidazole, benzimidazole and picoline.

13. A process as set forth in claim 10 wherein an additional amount of an organic base is introduced into said intermediate reaction product mixture to promote the reaction of 3-(methylthio)propanal with hydrogen cyanide.

14. A process set forth in claim 13 wherein the organic base introduced into the intermediate reaction product mixture comprises at least one organic base selected from the group consisting of imidazole, benzimidazole, 2-fluoropyridine, 4-dimethylaminopyridine, picoline and pyrazine.

15. A process as set forth in claim 13 wherein the organic base introduced into the intermediate reaction product mixture is the same organic base which comprises said olefin/mercaptan addition reaction catalyst used in reacting said methyl mercaptan with said acrolein.

16. A process as set forth in claim 13 wherein the organic base introduced into the intermediate reaction product mixture is pyridine.

17. A process as set forth in claim 13 wherein prior to the introduction of said additional amount of an organic base, said intermediate reaction product mixture contains between about 0.01 and about 1 weight percent of said organic base, and after said additional amount of an organic base is introduced into said intermediate reaction product mixture, said intermediate reaction product mixture contains between about 0.05 and about 1 weight percent of said organic base.

* * * * *